US009919136B2

(12) United States Patent
Lim et al.

(10) Patent No.: US 9,919,136 B2
(45) Date of Patent: Mar. 20, 2018

(54) CATHETER ASSEMBLY WITH REUSABLE VALVE

(71) Applicant: B. BRAUN MELSUNGEN AG, Melsungen (DE)

(72) Inventors: Siew Ping Lim, Penang (MY); E-Jen Teh, Penang (MY); Soo Yong Tan, Penang (MY); Teng Sun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 126 days.

(21) Appl. No.: 14/550,398

(22) Filed: Nov. 21, 2014

(65) Prior Publication Data
US 2015/0151088 A1 Jun. 4, 2015

Related U.S. Application Data

(60) Provisional application No. 61/911,904, filed on Dec. 4, 2013.

(51) Int. Cl.
*A61M 25/06* (2006.01)
*A61M 39/24* (2006.01)
(Continued)

(52) U.S. Cl.
CPC .... *A61M 25/0693* (2013.01); *A61M 25/0097* (2013.01); *A61M 25/0606* (2013.01); *A61M 2039/0036* (2013.01)

(58) Field of Classification Search
CPC ................. A61M 39/00; A61M 39/02; A61M 2039/0036; A61M 39/10;
(Continued)

(56) References Cited

U.S. PATENT DOCUMENTS 5,154,703 A * 10/1992 Bonaldo ............... A61M 39/14
604/202
5,487,728 A * 1/1996 Vaillancourt ......... A61M 39/26
604/167.02
(Continued)

FOREIGN PATENT DOCUMENTS

WO    WO 2012/009027 A1    1/2012
WO    WO 2015/017136 A1    2/2015

*Primary Examiner* — Quynh-Nhu H Vu
(74) *Attorney, Agent, or Firm* — Klein, O'Neill & Singh, LLP

(57) ABSTRACT

A catheter assembly includes a catheter hub having an elastomeric septum that divides the catheter hub into a distal chamber and a proximal chamber. The septum also includes at least one slit that is closed and sealed when the septum is in an at-rest state. A septum activator is proximal the septum. When an external force pushes the activator against the septum, the activator deforms the septum so as to break the seal and create a flow path through the septum. A portion of the septum activator can be collapsible when subjected to the outside force. When the outside force is removed, the collapsible portion springs back to its at-rest shape, helping to pull the activator out of deforming engagement with the septum so that the septum can reseal. The activator can also be spring-biased away from engagement with the septum so that when the outside force is removed, the spring urges the activator out of engagement with the septum. With the activator removed, the septum slit can reseal.

13 Claims, 19 Drawing Sheets

(51) Int. Cl.
*A61M 25/00* (2006.01)
*A61M 39/00* (2006.01)

(58) Field of Classification Search
CPC .. A61M 2039/0081; A61M 2039/0653; A61M 2039/066; A61M 2039/2433
See application file for complete search history.

(56) References Cited

U.S. PATENT DOCUMENTS

| | | | | |
|---|---|---|---|---|
| 5,613,663 | A * | 3/1997 | Schmidt | A61M 39/26 251/149.2 |
| 5,817,069 | A * | 10/1998 | Arnett | A61M 39/0606 251/149.1 |
| 5,967,490 | A | 10/1999 | Pike | |
| 6,595,981 | B2 * | 7/2003 | Huet | A61M 39/26 604/523 |
| 6,964,406 | B2 * | 11/2005 | Doyle | A61M 39/045 251/149.3 |
| 8,277,424 | B2 * | 10/2012 | Pan | A61M 39/26 604/249 |
| 8,357,119 | B2 | 1/2013 | Stout et al. | |
| 8,758,306 | B2 * | 6/2014 | Lopez | A61M 39/10 604/247 |
| 9,028,425 | B2 * | 5/2015 | Burkholz | A61B 5/1405 600/577 |
| 9,101,748 | B2 * | 8/2015 | Harding | A61M 39/0613 |
| 9,138,572 | B2 * | 9/2015 | Zeytoonian | A61M 39/045 |
| 2005/0256461 | A1 * | 11/2005 | DiFiore | A61M 25/0075 604/247 |
| 2008/0108944 | A1 * | 5/2008 | Woehr | A61B 5/1411 604/164.08 |
| 2012/0016301 | A1 | 1/2012 | Stout | |
| 2013/0030386 | A1 | 1/2013 | Panian et al. | |
| 2013/0165867 | A1 * | 6/2013 | Isaacson | A61M 25/0097 604/256 |
| 2015/0038910 | A1 | 2/2015 | Harding et al. | |

* cited by examiner

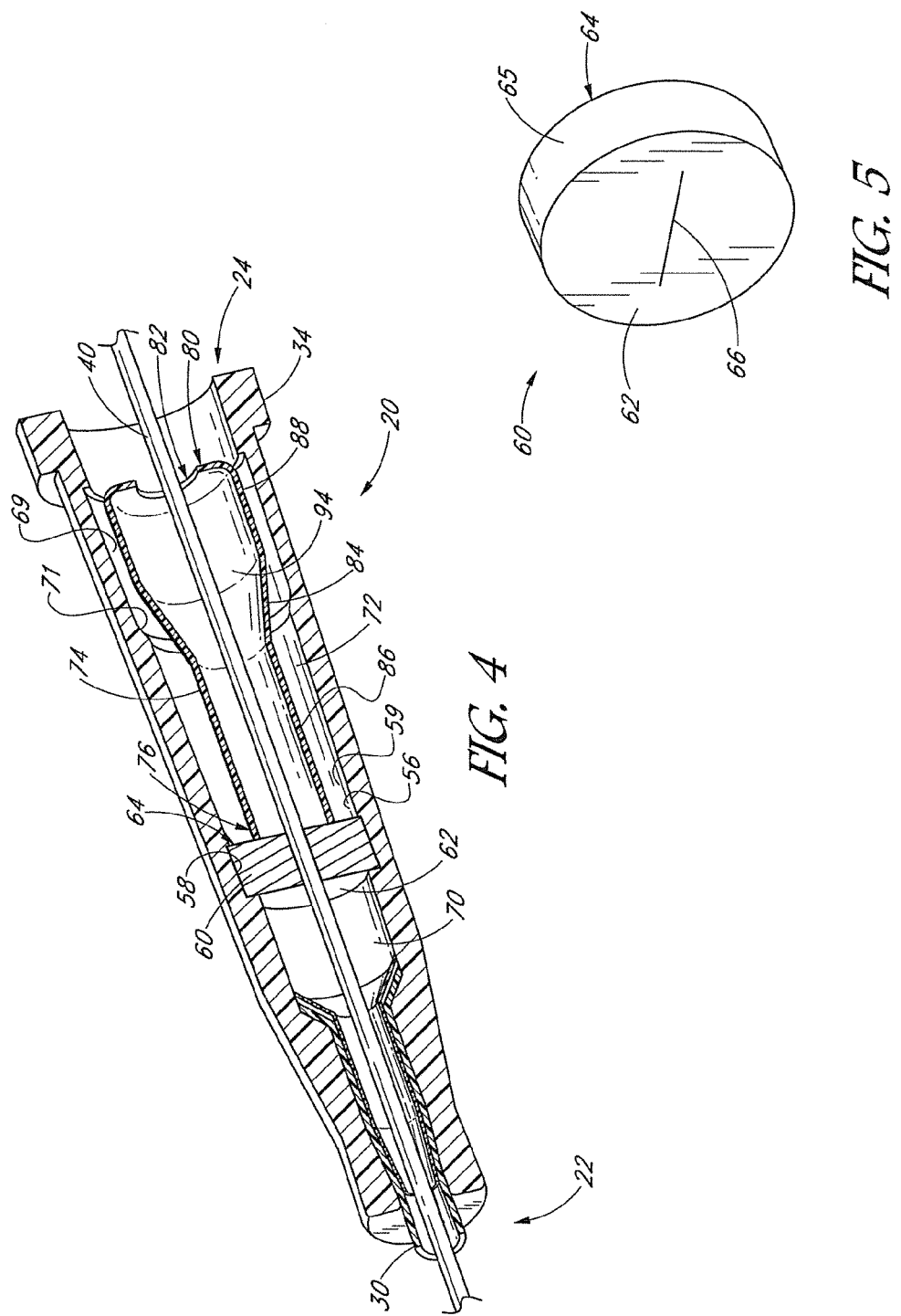

CATHETER ASSEMBLY WITH REUSABLE VALVE

CROSS-REFERENCE TO RELATED APPLICATIONS

The application claims priority to U.S. Provisional Application No. 61/911,904, which was filed on Dec. 4, 2013, the entirety of which is hereby incorporated by reference.

BACKGROUND

The present disclosure relates to the field of infusion devices, and more particularly to peripheral intravenous (IV) catheters.

A catheter assembly for an IV catheter generally includes a flexible catheter, or catheter tube, coupled to a distal end of a catheter adapter, which can include a catheter hub. The catheter adapter retains the catheter tube so that other components can interact with the catheter tube. In order to place the catheter tube in the patient's blood vessel, an introducer needle is coupled to the catheter adapter so that the needle extends through the catheter adapter and catheter tube, with the sharp distal tip of the needle positioned just beyond the distal end of the catheter tube. The clinician uses the introducer needle to penetrate the patient's tissue and place the distal end of the catheter tube in a blood vessel.

Once the needle tip and the catheter tube are in the vessel, the clinician typically uses blood flashback to confirm that placement is correct. For example, when the needle tip and/or the catheter tube is properly placed in the vasculature of the patient, blood from the vessel may flow through the needle and/or the catheter tube into the catheter adapter. When the clinician sees the blood in the catheter adapter, the clinician knows that the distal tip of the needle and/or the distal end of the catheter tube is in place in the blood vessel. Once it is verified that the catheter is correctly placed in the blood vessel, the introducer needle is removed.

During blood flashback, blood may accumulate in the catheter tube and catheter adapter. A valve such as an elastomeric septum in the catheter adapter contains the blood in a distal chamber of the catheter adapter. It can be desired to selectively open the septum to, for example, obtain a blood sample or to deliver IV fluids to the patient. Typically a septum activator is arranged proximal the septum. When the septum activator is forced into the septum, the septum is deformed and opened, creating a flow path for collection of a blood sample or delivery of IV fluids.

In some instances it is desirable to have a reusable septum and septum activator so that the septum activator can be disengaged from the septum, and the septum will again seal, but forcing the septum activator into the septum at a later time will again break the seal and create a fluid flow path.

SUMMARY

Accordingly, there is a need in the art for a catheter adapter having a septum or valve and an associated septum activator that accommodate repeated opening and resealing of the septum.

In accordance with a preferred embodiment, the present disclosure provides a catheter assembly, comprising a catheter adapter defining an internal space. A septum within the internal space divides the internal space into a distal chamber and a proximal chamber. A septum activator has a compressible portion that is configured to be compressed from an at rest configuration to a compressed configuration when a coupler contacts and applies a force to a proximal end of the septum activator so as to urge the septum activator into the septum so as to deform the septum. When the coupler is removed from contact with the septum activator, the compressible portion elastically expands to the at rest configuration so as to generate a return force urging the septum activator proximally.

In some such embodiments, the septum activator can have a plurality of elongate, spaced apart legs. For example, the septum activator can have a pair of, three, or more spaced apart legs that are configured to deflect when the coupler applies the force to the septum. Also, in some embodiments, the spaced apart legs can extend a majority of the length of the septum activator.

Another embodiment can comprise a method in which attaching a coupler to a catheter adapter applies a force to the septum activator and both elastically compresses a compressible portion of septum activator and forces the septum activator into the septum so as to deform the septum. Removing the coupler frees the septum activator to elastically return to its non-compressed state, generating a return force urging the septum activator proximally relative to the septum.

In accordance with another embodiment, a catheter assembly comprises a catheter adapter defining an internal space. A septum activator within the internal space has a proximal end and is movable between a proximal at rest position and a distal actuated position. A stationary arm extending from an inner wall of the catheter adapter is adjacent the septum activator. A movable member is configured to move with the septum activator within the catheter adapter internal space. A spring is interposed between the stationary arm and a portion of the movable member. The spring is configured to bias the septum activator toward the at rest position.

In some such embodiments, the movable member can be integrally formed with the septum activator. In other embodiments, the movable member can be formed separately formed the septum activator.

In some additional embodiments the spring can be arranged so that when the movable member is moved distally relative to the catheter adapter, the spring is compressed between the movable member and the stationary arm. In some such embodiments, the spring may not be directly attached to the stationary arm, and in further embodiments the spring can be directly attached to the movable member.

In yet additional embodiments, the spring can be arranged so that when the movable member is moved distally relative to the catheter adapter, the spring is stretched between the movable member and the stationary arm.

In some embodiments, the septum activator can be configured to be urged from the at rest position distally to the actuated position when a coupler extension applies a force to a proximal end of the septum activator.

In accordance with still another embodiment, the present disclosure provides a catheter assembly comprising a catheter adapter defining an internal space, and a septum activator defining a septum activator lumen and having a proximal side opening formed through a side wall of the septum activator. A blood flashback chamber can be defined between the septum activator side wall and an inner surface of the catheter. A one-way valve is provided at the proximal side opening. The one-way valve enables a distally-directed fluid flow to flow therethrough from the septum activator lumen into a space between the septum activator and the inner surface of the catheter adapter so that the distally-directed fluid flow can flush blood in the flashback chamber in a distal direction and out of the catheter adapter.

In some such embodiments, the one-way valve can comprise a hinged flap.

In yet additional embodiments, the one-way valve can comprises a hydrophobic surface.

In still further embodiments, a distal side wall can be formed through the side wall of the septum activator and spaced distally from the proximal side wall.

In still additional embodiments, the septum activator can comprise an inner tubular body and an outer tubular body that are movable relative to one another between a blocked arrangement and an aligned arrangement. Proximal and distal side openings formed through side walls of each of the inner and outer tubular bodies being aligned when the bodies are in the aligned arrangement. In some such embodiments, the one-way valve can be placed over one or the other of the proximal side openings of the inner and outer tubular bodies. In further embodiments, the one-way valve can be limited to only the proximal side openings.

Further additional embodiments can involve methods of using and/or making any of the embodiments described herein.

BRIEF DESCRIPTION OF THE DRAWINGS

FIG. 4 is a cutaway view showing a catheter adapter with an introducer needle extending therethrough;

FIG. 5 is a perspective view of a septum for use in the catheter adapter of FIG. 4;

DESCRIPTION

Figure 1:
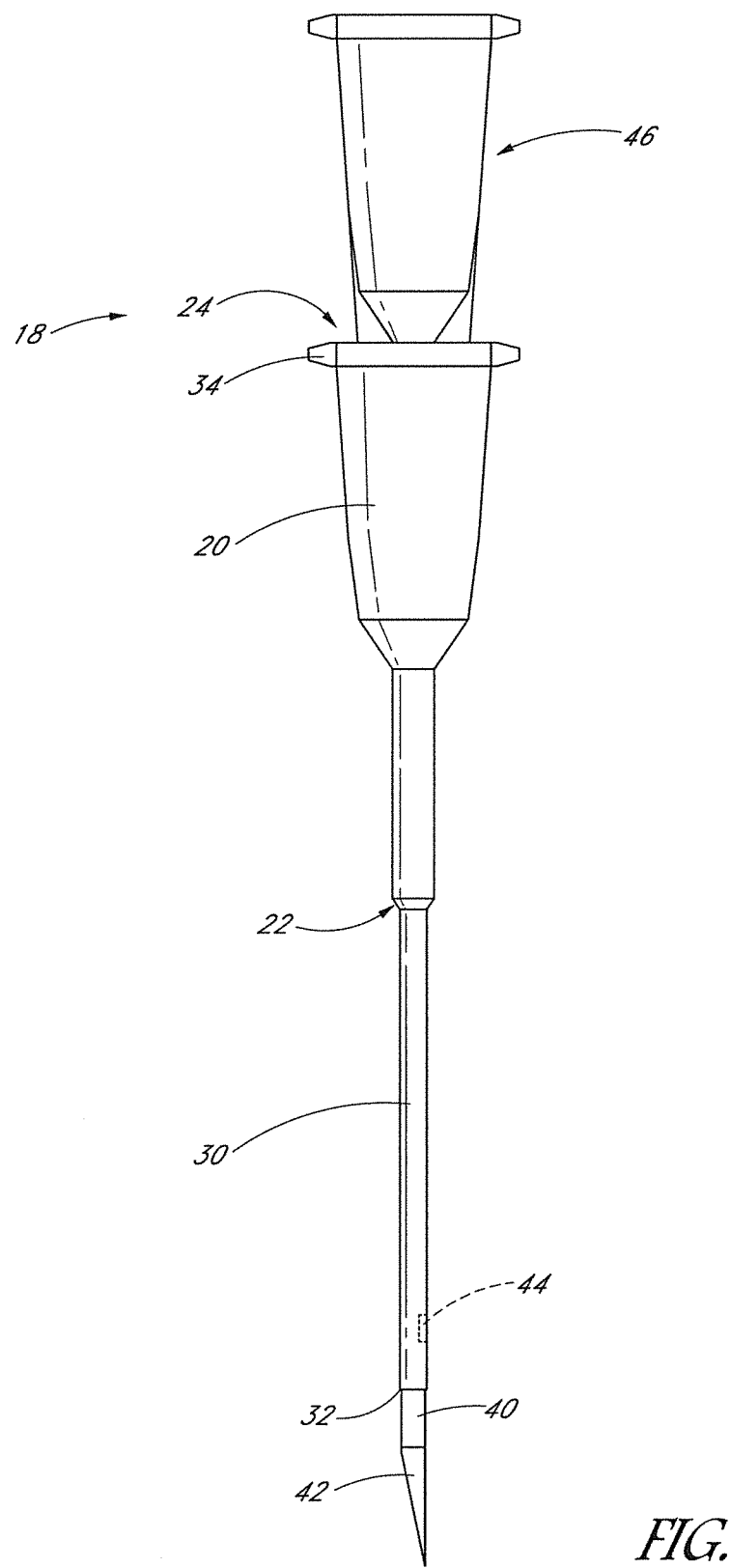
FIG. 1 shows a schematic view of a catheter assembly having features in accordance with the present disclosure.

With initial reference to FIG. 1, an embodiment of a catheter assembly 18 is shown. The catheter assembly 18 includes a catheter adapter 20, also sometimes referred to as a catheter hub, having a distal end 22 and a proximal end 24. A catheter tube 30 extends from the distal end 22 of the adapter and terminates at a catheter distal end 32. A flange 34, which may comprise threads, at the proximal end 24 of the catheter adapter 20 is configured to releasably accommodate other components, such as a coupler for coupling IV fluid tubing in a luer fit or threaded arrangement.

Figure 2:
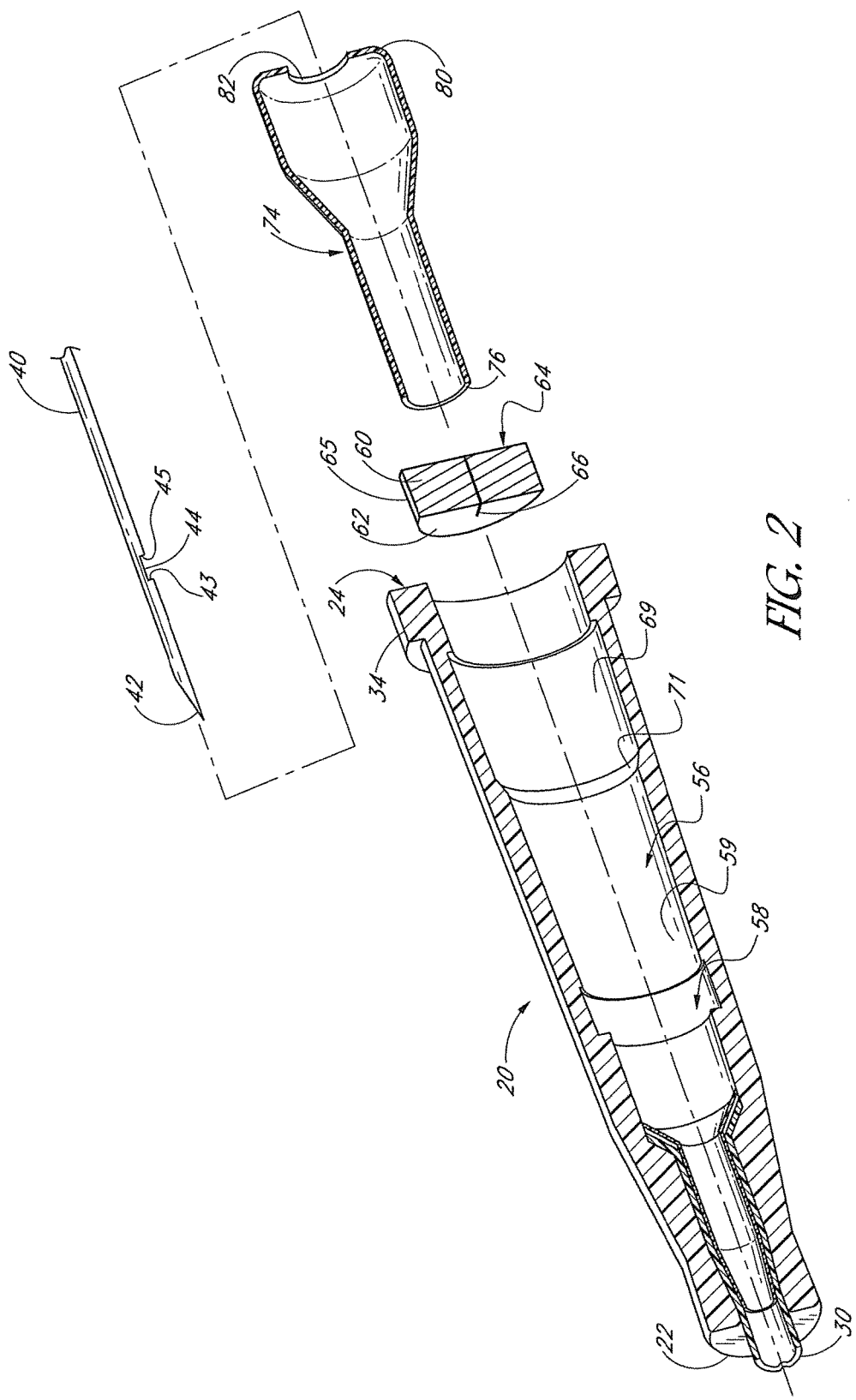
FIG. 2 is an exploded, cutaway view of the catheter assembly of FIG. 1.

As shown, and with additional reference to FIG. 2, an introducer needle 40 has a hollow distal tip 42. In the illustrated embodiment, an outlet aperture 44 in the form of (or as part of) a notch is formed through a side of the introducer needle 40 proximal the distal tip 42. In the illustrated embodiment, the aperture 44 is elongated and has a distal end 43 and a proximal end 45. The aperture 44 can be formed in various ways and by conventional means, including by crimping the needle and forming an aperture in part or all of the crimped portion. A needle hub 46 is engaged with the proximal end 24 of the catheter adapter 20. The introducer needle 40 extends from the hub 46 through the catheter adapter 20 and the catheter tube 30 so that its distal tip 42 is disposed just distal of the distal end 32 of the catheter tube 30.

With reference next to FIGS. 2-5, the catheter adapter 20 defines an internal lumen 56 extending from the proximal end 24 to the distal end 22. A septum seat 58 is formed in an inner wall 59 of the catheter adapter 20. A valve, which can be in the form of an elastomeric septum 60, preferably is configured to fit in the septum seat 58 so as to sealingly engage the inner wall 59 of the catheter lumen 56 at the septum seat 58. The illustrated septum 60 has a distal face 62, a proximal face 64, and a circumferential surface 65. At least one slit 66 is formed through the septum 60 so that the septum 60 can be selectively deformed in order to open the slit and break the seal. Also, preferably the introducer needle 40 can extend through the slit 66, but edges of the slit 66 will engage the outer wall of the needle so as to maintain a full or partial sealing engagement with the needle 40.

As best shown in FIG. 4, a distal chamber 70 is defined within the catheter adapter lumen 56 distal of the septum 60. A proximal chamber 72 is defined proximal of the septum 60.

Figure 3:
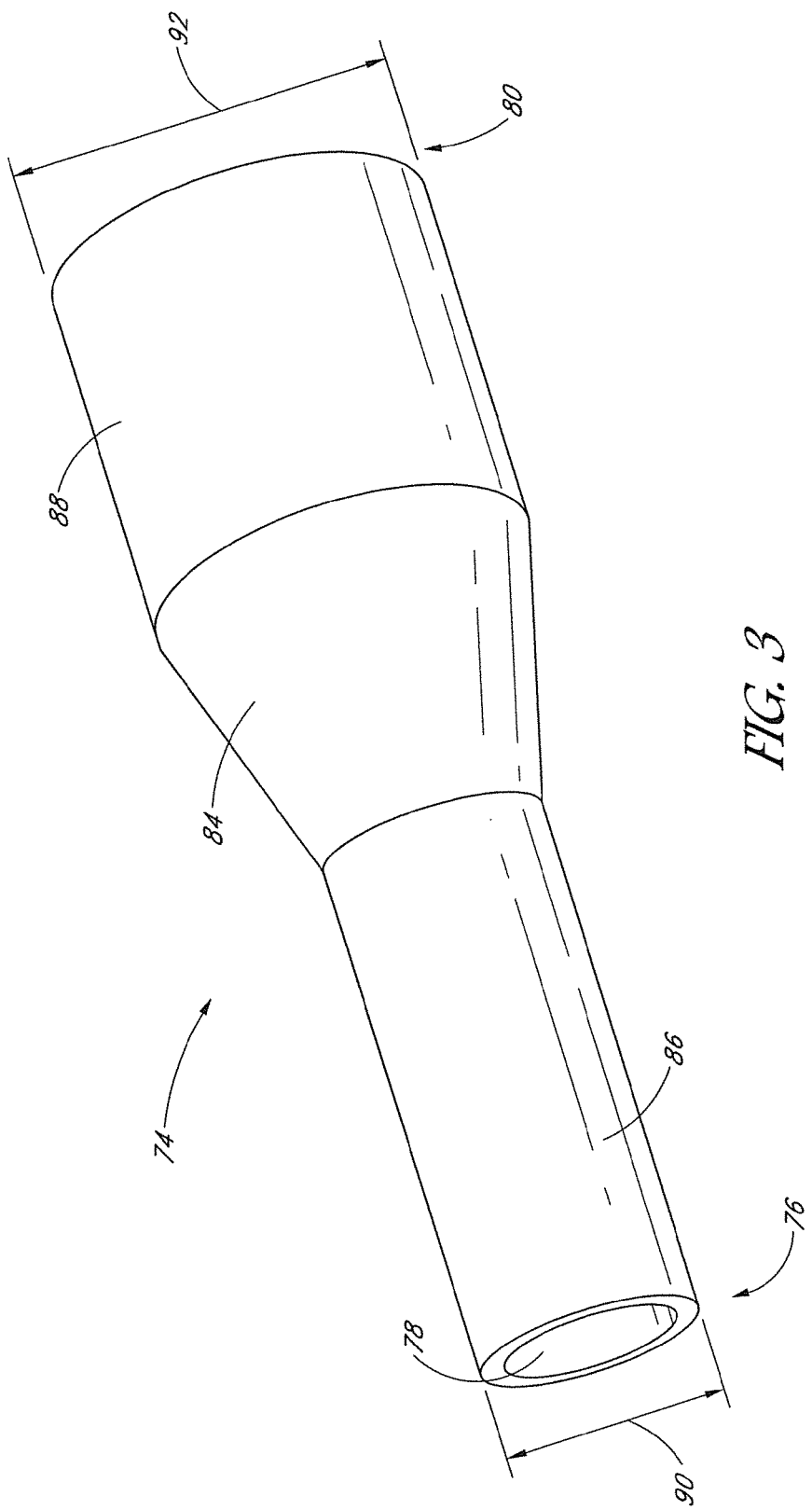
FIG. 3 is a perspective view of a septum activator in accordance with one embodiment.

With continued reference to FIGS. 2-4, a septum activator 74 has a distal end 76 at which a distal opening 78 is formed, and a proximal end 80 at which a proximal opening 82 is formed. The illustrated septum activator 74 has a transition section 84 disposed between the distal section 86 and a proximal section 88. A diameter of the septum activator 74 increases moving proximally through the transition section 84 so that a proximal diameter 92 of the septum activator is greater than a distal diameter 90. An activator lumen 94 is defined within the septum activator.

As best shown in FIG. 4, when the catheter assembly is assembled, the septum activator 74 preferably is disposed within the proximal chamber 72 of the catheter adapter 20 so that the distal end 76 of the activator 74 is adjacent the proximal face 64 of the septum 60, and the introducer needle 40 extends through the activator lumen 94. Although not shown, the septum activator may include guides or fins along an exterior thereof for aligning to the catheter lumen to limit yawing and pitching. In the illustrated embodiment, an expansion groove 69 or cavity is formed in the proximal chamber 72 of the catheter adapter 20, and the proximal section 88 of the activator 74 is adjacent the expansion groove 69. The expansion groove 69 enlarges a nominal interior diameter of the catheter adapter to provide a space into which the septum activator 74 can expand. In some examples, the expansion groove is located distally of a luer inlet section of the catheter adapter and has an interior diameter larger than the luer inlet.

With the catheter assembly 18 assembled as illustrated in FIGS. 1 and 4, the catheter assembly 18 is ready to be placed into a patient's blood vessel. In use, the clinician penetrates the patient's tissue using the distal tip 42 of the needle 40. Once the distal tip 42 is in the blood vessel, blood will flow into the needle 40 at the tip 42 and out the aperture 44 into the catheter tube 30 and/or catheter adapter 20. Blood can also flow into the interior cavity of the needle hub, which typically has a vent plug to prevent spilling out the needle hub. Blood flashback can be expected to at least partially fill the distal chamber 70 of the catheter adapter 20. In some embodiments, air vents may be formed through or around the septum 60 so as to relieve positive air pressure that may tend to resist blood flashback. In additional embodiments, the needle may not have an aperture, and flashback blood will flow through the needle to the needle hub, which may include a viewing port so the clinician can see flashback blood so as to verify that the needle tip has entered the blood vessel. Further, in some embodiments, after the clinician sees blood in the needle hub viewing port, the clinician advances the catheter tube over the needle until blood flows through the catheter tube and into the distal chamber 70, verifying that the distal end 32 of the catheter tube 30 has entered the blood vessel.

Once the catheter tube 30 is verified to be properly positioned with its distal end 32 in the patient's blood vessel, the introducer needle 40 can be removed. With the needle 40 removed, the septum 60 slit 66 closes, and preferably fully seals.

Figure 6:
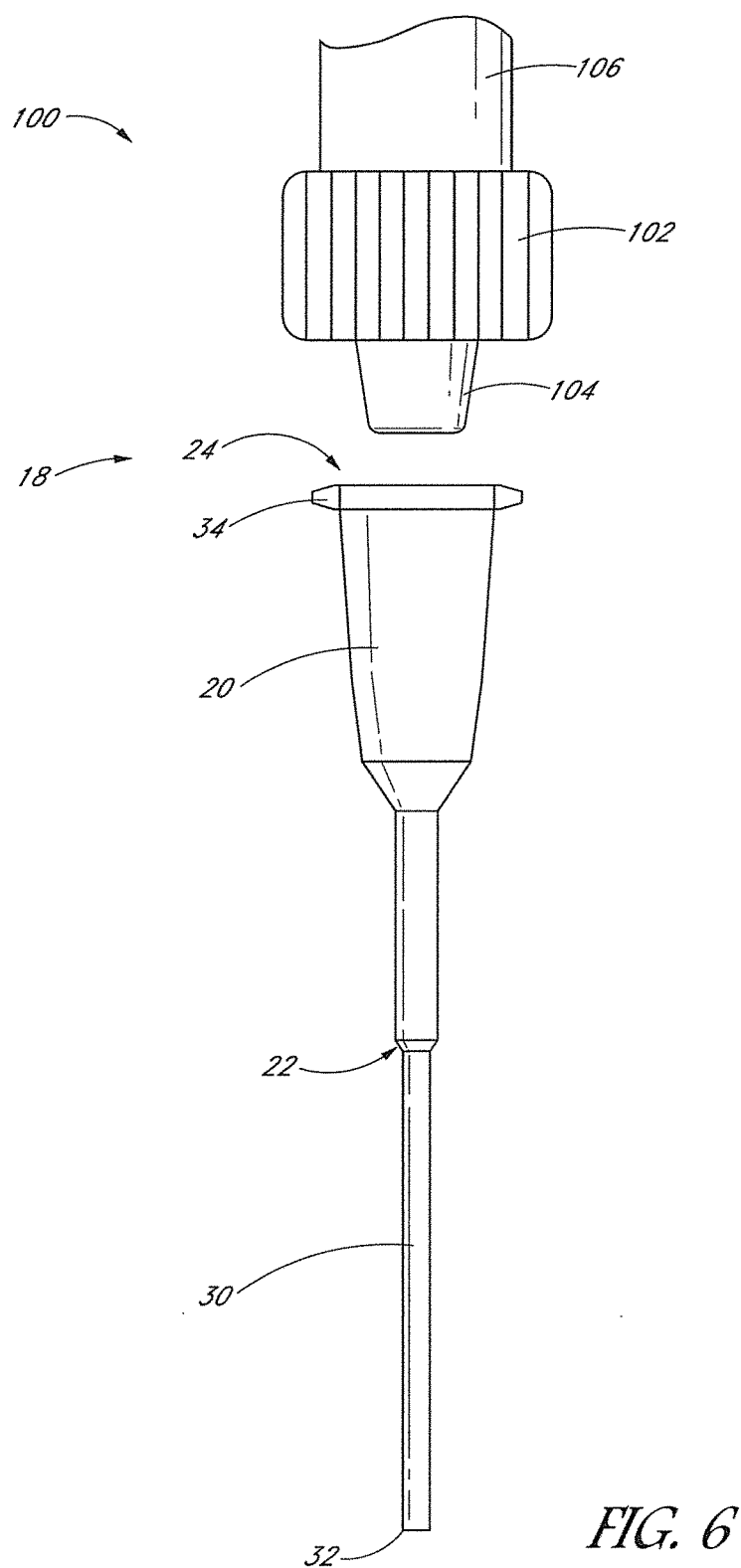
FIG. 6 shows the catheter adapter of FIG. 1 with an external coupler about to be connected.
Figure 7:
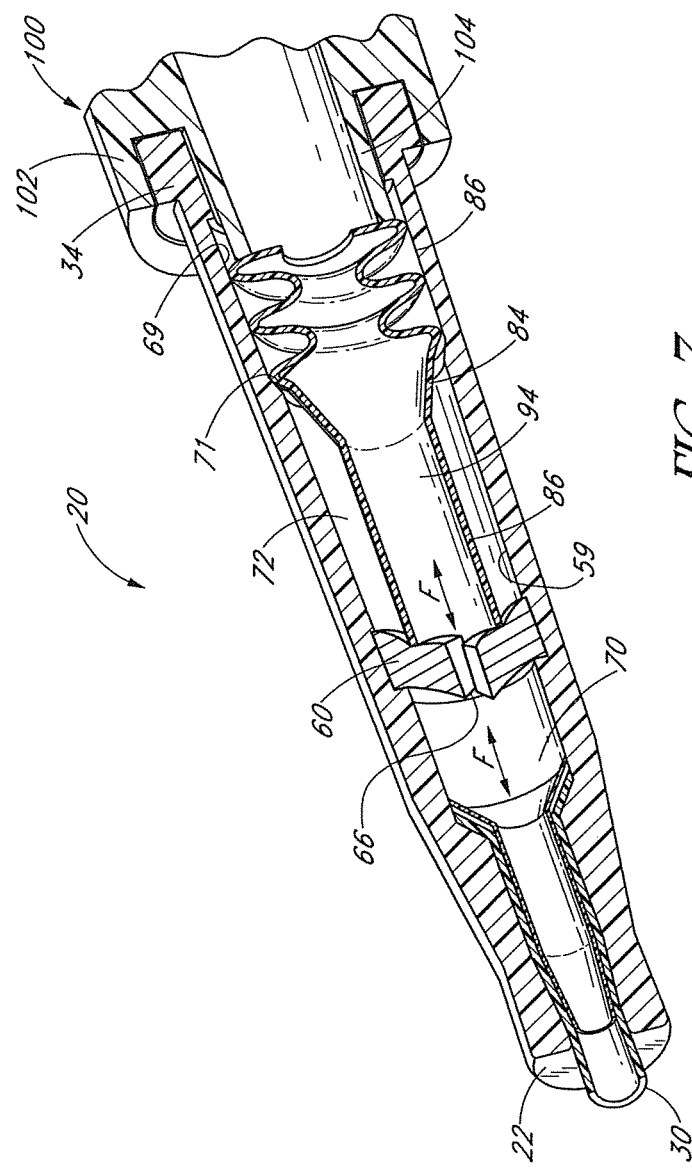
FIG. 7 shows the arrangement of FIG. 4 with a connector engaged.

With reference next to FIGS. 6 and 7, in some embodiments, after the introducer needle 40 has been removed a conduit coupler, such as a luer connecter 100, can be connected to catheter adapter 20. The illustrated coupler 100 comprises a nut or threaded collar 102 that threadingly engages the flange 34. An extension 104, such a male luer tip, extends distally from the nut 102 into the proximal chamber 72 of the catheter adapter 20, which can have a female luer. The illustrated coupler 100 communicates with a tube 106 or has a hub body that communicates with a tube. The tube 106, in turn, may be, or may be connected to, a source of IV fluids, a blood sample collection apparatus such as a vacuum tube or syringe, or other medical treatment delivery or collection devices as desired.

During coupling of the conduit coupler 100 with the flange 34, the extension 104 enters the proximal chamber 72, and may engage and apply a distally-directed force to the proximal end 80 of the septum activator 74, thus pushing the septum activator 74 distally to deform the septum 60. As such, the slit 66 opens to form one or more fluid pathways F through the septum 60. If the tube 106 communicates with a medical delivery device, such as a source of IV fluids, such IV fluids can then be delivered along the flow path into the catheter adapter 20, through the open septum 60 and into the catheter tube 30 for delivery to the patient's blood vessel. Such IV fluids may also flush blood out of the distal chamber 70. If the tube 106 communicates with or comprises a medical collection device, such as a blood sample collection tube or syringe, blood from the patient's blood vessel can then be aspirated along the flow path from the distal chamber 70 through the open septum 60 and into the tube 106 for collection. Preferably, after aspiration of blood, a fluid delivery device is connected via a coupler 100 and fluid is delivered to flush residual blood from inside surfaces of the activator and catheter adapter.

In FIG. 7, the proximal section 88 of the septum activator 74 comprises an elastically compressible portion, so that the distally-directed force applied by the coupler extension 104 compresses the proximal section 88, which in the illustrated embodiment collapses or folds over itself. Various structural compositions may be employed to make the proximal section 88 elastically compressible. For example, the proximal section 88 may be constructed of a different material than the distal and transition sections 86, 84 of the activator 74. For example, the distal and transition sections 86, 84 may be constructed of a medical-grade rigid or semi-rigid plastic, while the compressible portion of the proximal section 88 may have a reduced thickness, may be made of an elastomeric material, may be divided into different subsections alternating between elastomeric material and rigid or semi-rigid plastics, and/or may include other materials or hybrids of mixed materials.

Preferably, the compressible portion of the proximal section 88 is configured so that sufficient force is still communicated through the septum activator 74 to the septum 60 so as to deform the septum 60 and open the fluid pathway. With continued reference to FIG. 7, the expansion groove 69 receives at least a portion of the compressed proximal section 88. In the illustrated embodiment, at least a portion of the compressed proximal section 88 engages a distal end 71 of the expansion groove 69 and, preferably, a portion of the catheter adapter's inner wall 59 in the groove 69. The elastically-compressed portion of the proximal section 88 applies a force against the inner wall 59, including the distal end 71, in opposition to the distally-directed force applied by the coupler extension 104.

When the coupler 100 is removed, the deformed elastomeric septum 60 will exert a proximally-directed force that tends to urge the septum activator 74 proximally. Also, the elastically-compressed portion of the proximal section 88 will decompress. Preferably, as the elastically compressible portion decompresses it generates some momentum so that when the proximal section 88 reaches its relaxed state the momentum is transferred to the septum activator 74, providing an additional proximally-directed force to urge it out of engagement with the septum 60. As such, the septum 60 may reseal, and the septum activator 74 is again positioned proximal to the septum 60, ready to again engage and deform the septum 60 upon attachment of another coupler 100.

Figure 8A:
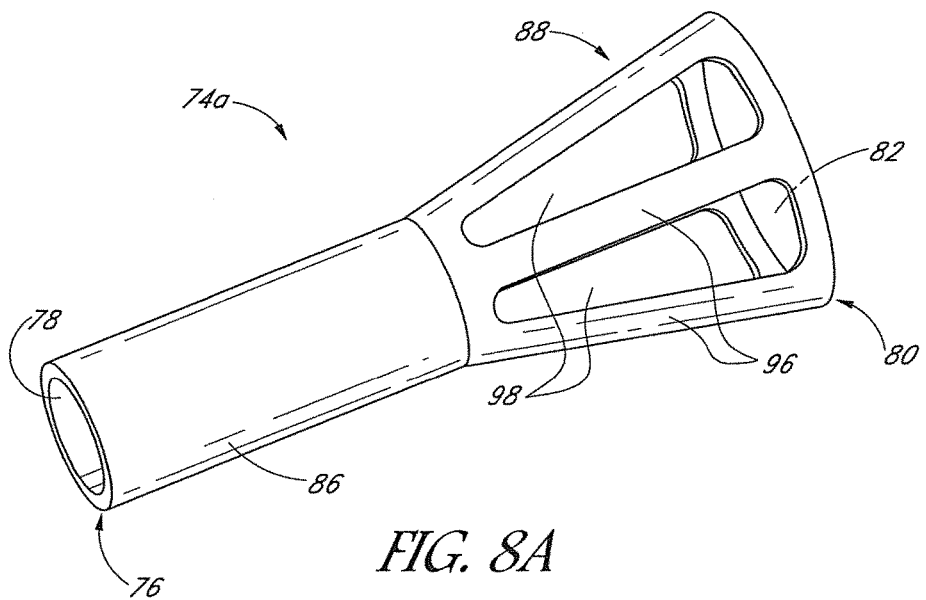
FIGS. 8A-8D shows additional embodiments of a septum activator.

With reference next to FIG. 8A, another embodiment of a septum activator 74a comprises three or more elongate legs 96 extending along a portion of the length of the septum activator. The illustrated legs are configured to function as a compressible portion, deflecting when the septum activator is engaged and forced distally by the coupler. Apertures 98 are formed between adjacent legs 96. The apertures 98 provide another path for fluid flow within the catheter adapter 20 and externally of the septum activator 74*a*. When the coupler 100 is removed, the deflected legs 96 spring back into their at-rest position, thus further urging the septum activator 74*a* proximally and out of engagement with the septum 60.

Figure 8B:
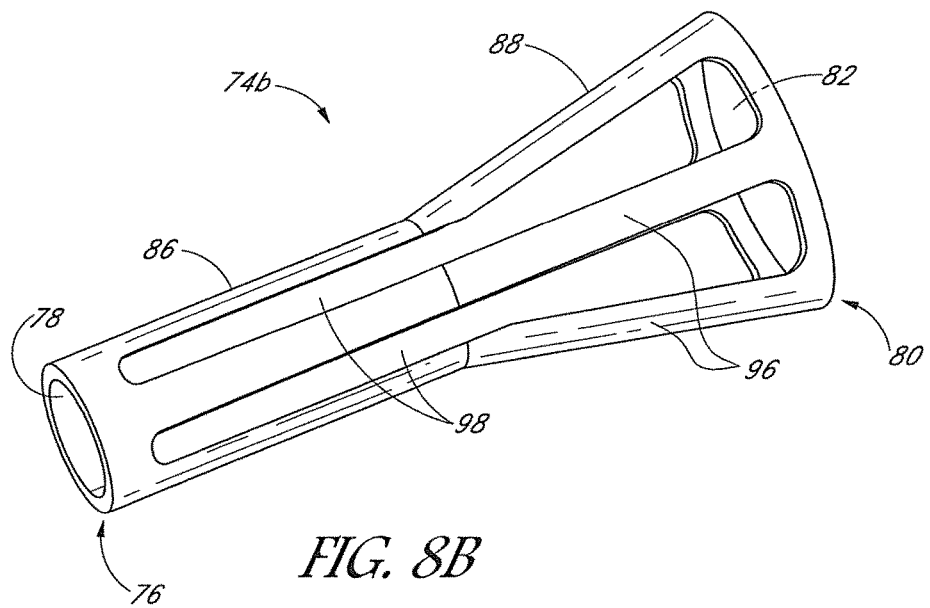
Figure 8C:
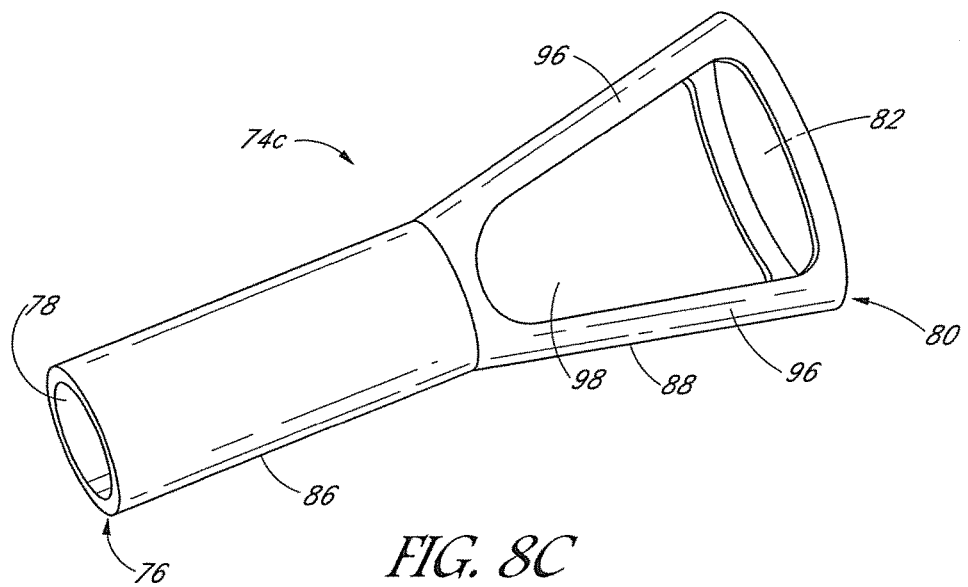
Figure 8D:
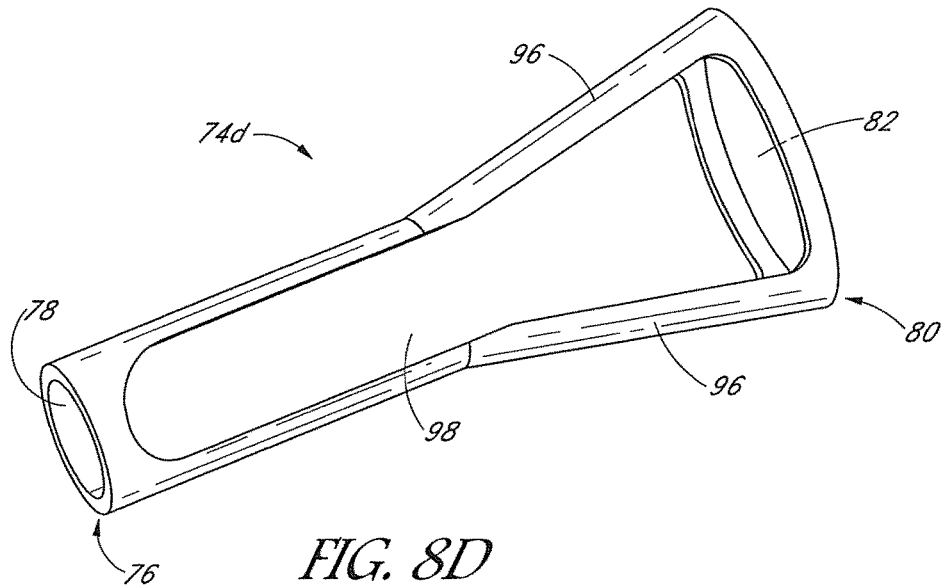

With reference next to FIG. 8B, another embodiment of a septum activator 74*b* also comprises at least three elongate legs 96, but the legs 96 extend along the majority of the length of the septum activator 74*b* and through the transition section 84 between the proximal portion and the distal portion. FIGS. 8C and 8D depict embodiments of septum activators 74*c*, 74*d* having only two elongate legs 96, and apertures between adjacent legs 96. Similar to the embodiment of FIG. 8B, the septum activator 74*d* of FIG. 8D incorporates elongate legs 96 that extend through the transition section between the distal and proximal sections of the activator. Still further embodiments may include more elongate legs, and may include legs of various cross-sectional shapes, stiffness values, materials, etc. In yet other embodiments, weakened or kinked sections may be incorporated with the septum actuator to define preferential collapsible sections when the septum actuator compressed by a male Luer.

Figure 9:
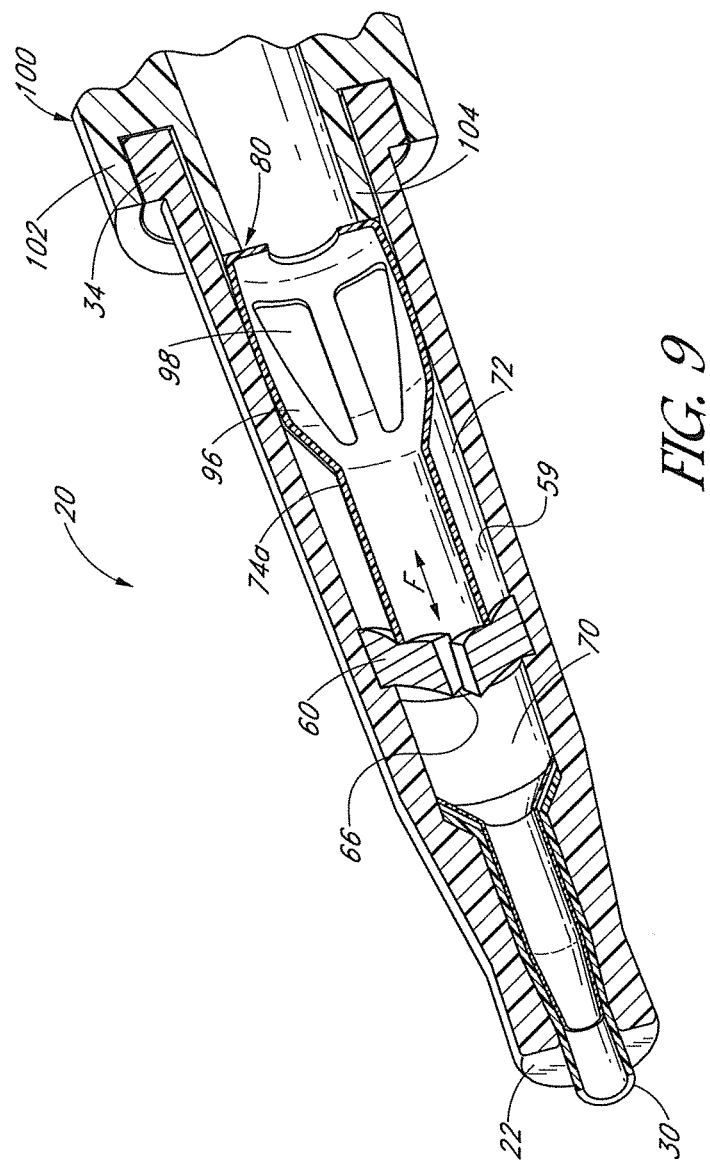
FIG. 9 is a cutaway view showing another embodiment of a catheter adapter employing the septum activator of FIG. 8A.

Referring next to FIG. 9, an embodiment is shown in which the septum activator 74*a* of FIG. 8A is disposed within a catheter adapter 20, to which a coupler 100 is attached. As in the embodiments discussed above, the extension 104 of the coupler 100 engages and applies a distally-directed force to the proximal end 80 of activator 74*a*, which in turn engages and deforms the septum 60 to establish a fluid flow path F. As shown, the legs 96 of the activator 74*a* are compressed by the distally-directed force. More specifically, the legs 96 are forced to bow outwardly, and preferably engage the inner wall 59 of the catheter adapter 20. Preferably at least the legs 96 of the activator 74*a* are formed of a compressible material or spring. When the distally-directed force applied by the coupler 100 is removed, the bowed legs 96 will tend to return to their at-rest position, and in the process will tend to urge the septum activator 74*a* proximally and out of engagement with the septum 60.

In the embodiment illustrated in FIG. 9, the catheter adapter 20 does not include an expansion groove as did the embodiment illustrated in FIG. 7. However, it is anticipated that additional embodiments can employ such an expansion groove or similar structure to accommodate the legs 96 when bowed outwardly.

Figure 10A:
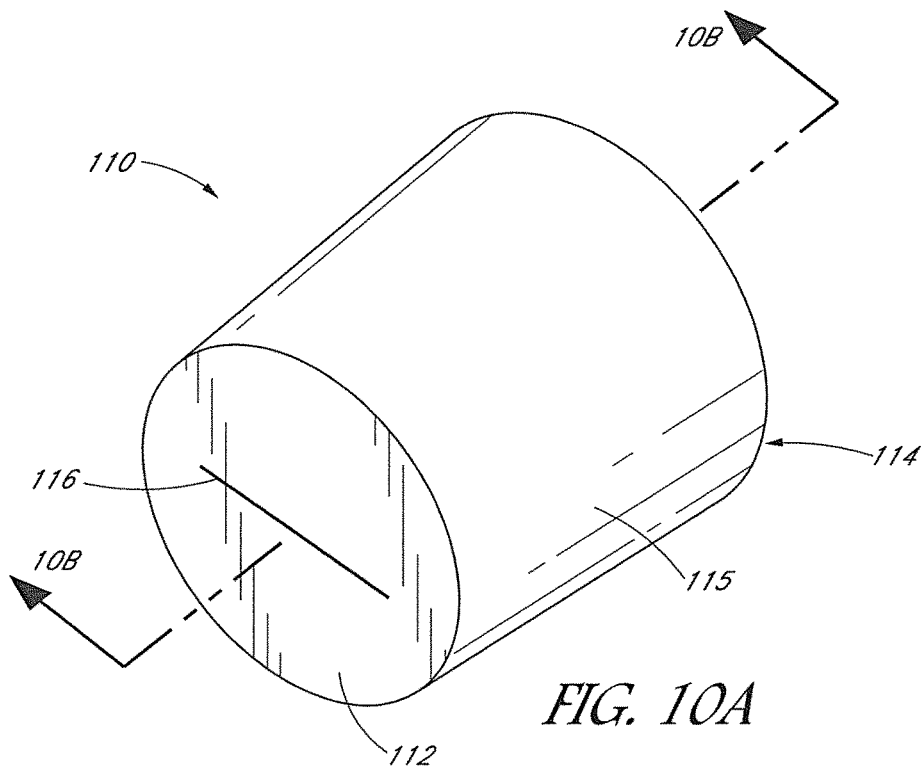
FIG. 10A is a perspective view of another embodiment of a septum.
Figure 10B:
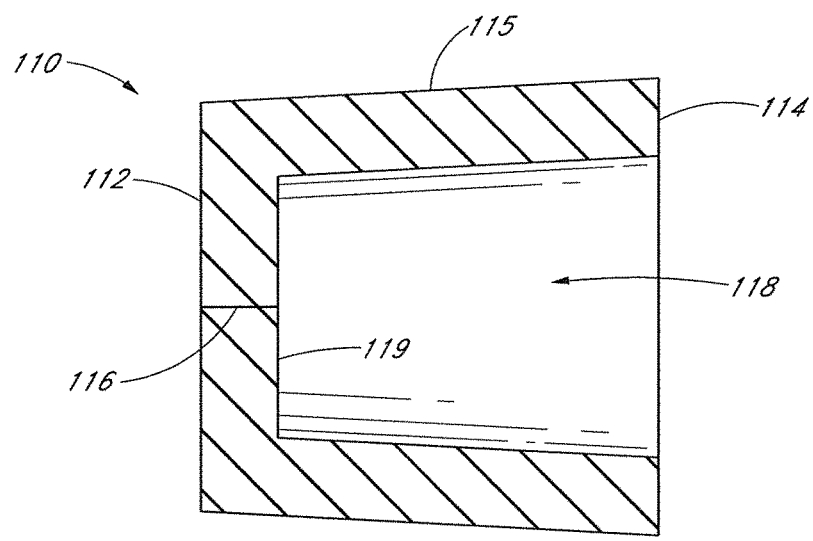
FIG. 10B is a cross-sectional view taken along line 10B-10B of FIG. 10A.

With reference next to FIGS. 10A and 10B, another embodiment of an elastomeric septum 110 is shown. The septum 110 includes a distal face 112, a proximal end 114, and a circumferential surface 115, which may also be referred to as a skirt, between the distal face 112 and proximal end 114. A central cavity 118 extends distally from the proximal end 114, terminating in a proximal face 119 opposite the distal face 112. At least one slit 116 extends through the septum 110 from the distal face 112 to the proximal face 119. In the illustrated embodiment, the septum 110 is slightly tapered so as to expand in diameter from the distal face 112 to the proximal end 114. Other embodiments may not employ such a taper.

Figure 11:
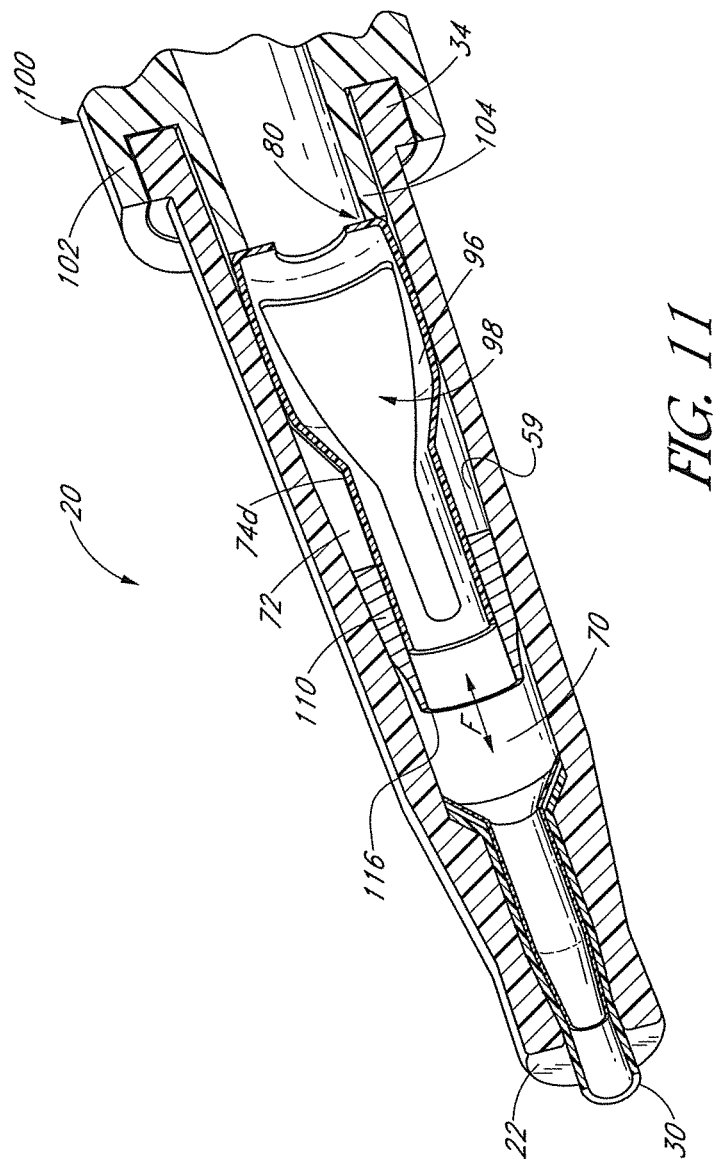
FIG. 11 is a cutaway view showing another embodiment of a catheter adapter employing the septum activator of FIG. 8D.

With reference next to FIG. 11, an embodiment is shown in which the septum activator 74*d* of FIG. 8D is disposed within a catheter adapter 20, to which a coupler 100 is attached. As in the embodiments discussed above, the extension 104 of the coupler 100 engages and applies a distally-directed force to the proximal end 80 of activator 74*d*, which in turn engages and deforms the septum 110 to establish a fluid flow path F. As shown, the legs 96 of the activator 74*d* are compressed by the distally-directed force, bowing the legs 96 outwardly and into engagement with the inner wall 59 of the catheter adapter 20. When the distally-directed force applied by the coupler 100 is removed, the bowed legs 96 will tend to return to their at-rest position, and in the process will tend to urge the septum activator 74*a* proximally and out of engagement with the septum 60.

In the illustrated embodiment, the inner wall 59 of the catheter adapter 20 is tapered and uninterrupted by any septum seat. It is to be understood, however, that additional embodiments may include a septum seat for receiving the septum 110 and/or an expansion groove for receiving at least a portion of the bowed-out legs 96.

It is also to be understood that embodiments as described herein may employ one or the other of the septums 60, 110 as described herein, or may employ septums having other specific structural configurations. Notably, the apertures 98 in the illustrated embodiment will enable flushing of blood that may have accumulated in both the distal and proximal chambers 70, 72 of the catheter adapter 20 when the coupler 100 attaches a source of flushing fluid such as an IV fluid.

Figure 12:
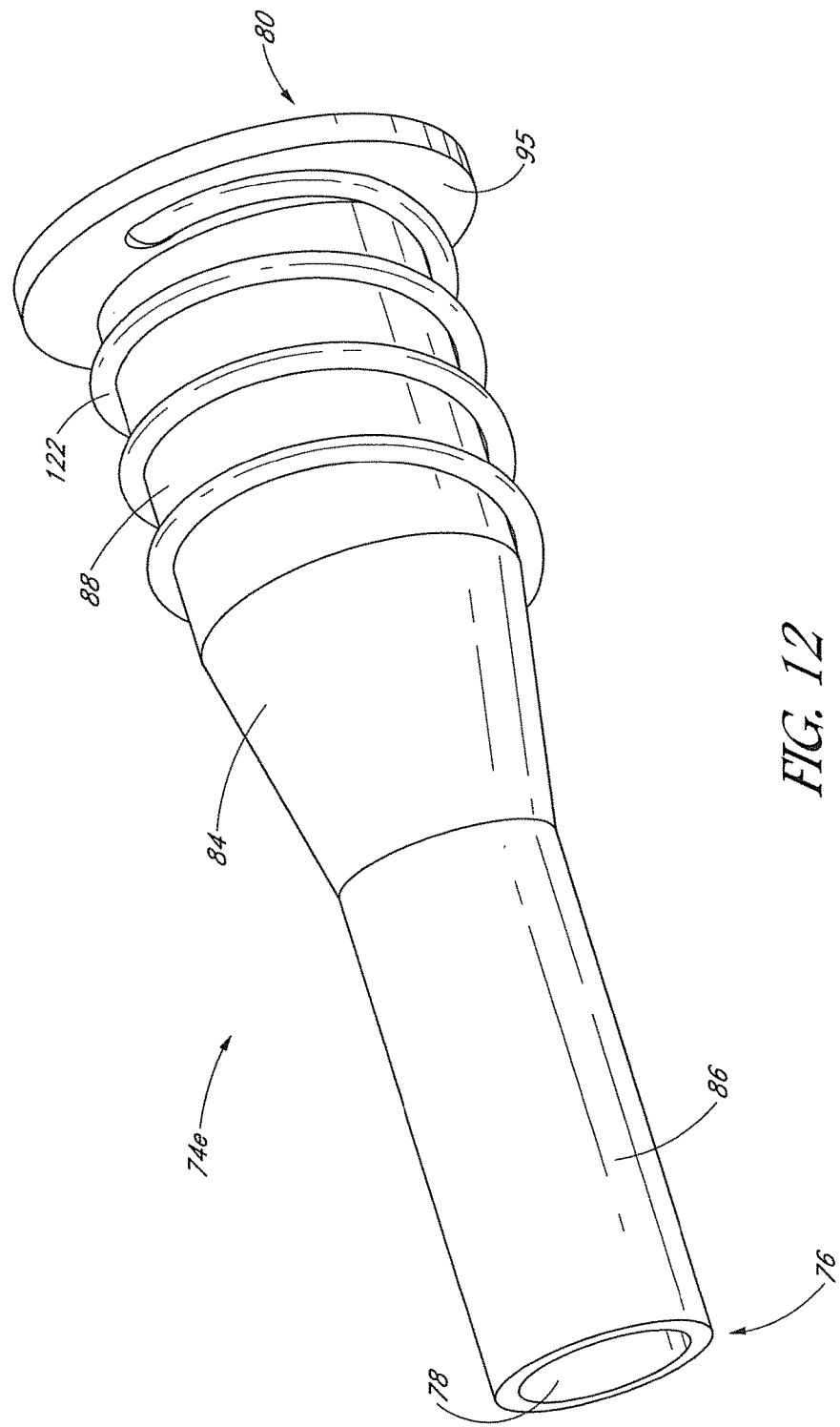
FIG. 12 is a perspective view of yet another embodiment of a septum activator.
Figure 13:
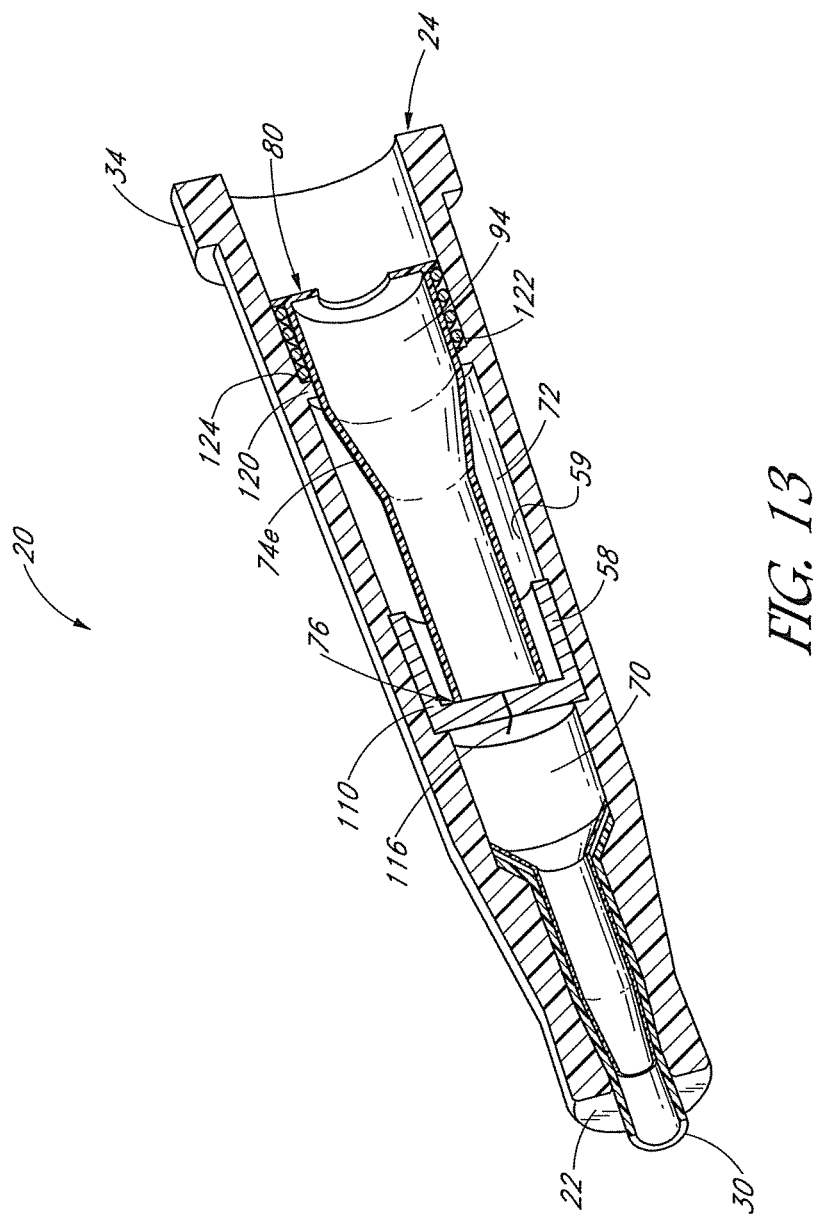
FIG. 13 is a cutaway view showing another embodiment of a catheter adapter employing the septum activator of FIG. 12.
Figure 14:
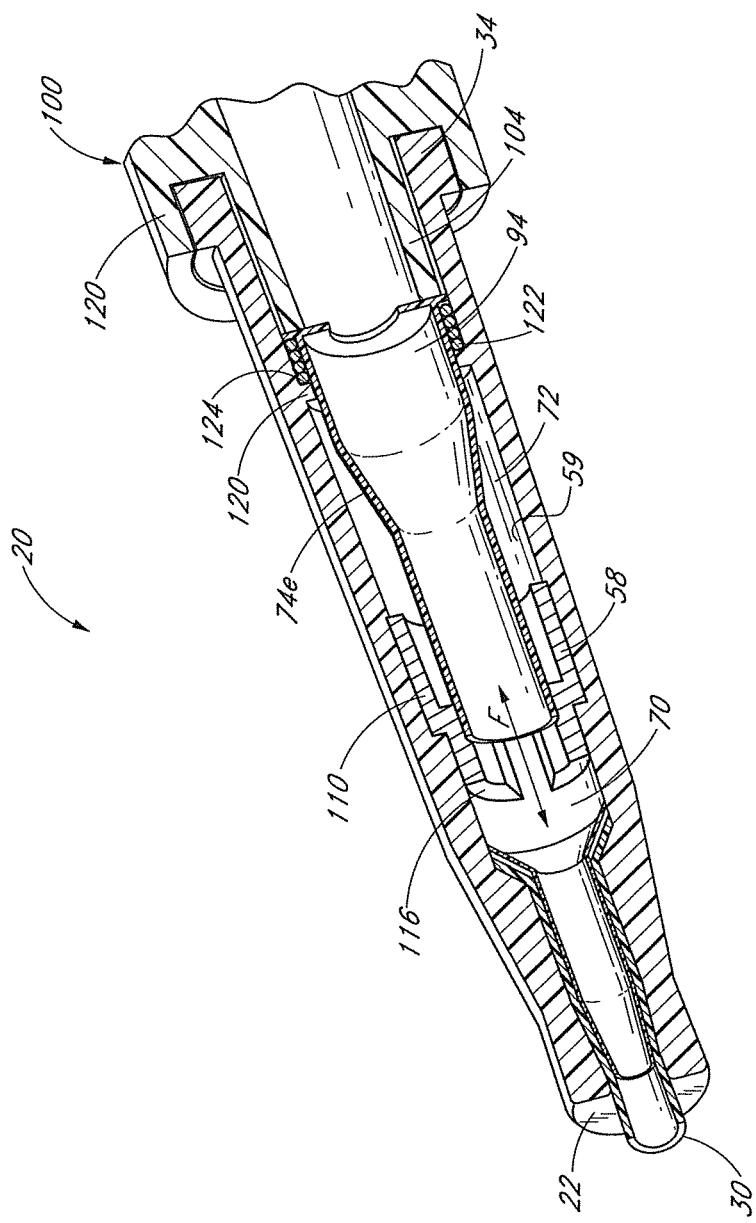
FIG. 14 shows the arrangement of FIG. 13 with a connector engaged.

With reference next to FIGS. 12-14, another embodiment is presented in which a stationary arm 120 (FIG. 13), such as an inward protruding rib, is connected to the inner surface 59 of the catheter adapter 20. Preferably the stationary arm 120 is in the form of a circumferential or partially-circumferential, inwardly-directed ridge unitarily formed as part of the catheter adapter 20. The illustrated septum activator 74*e* comprises an outwardly-directed proximal flange 95, to which a proximal end of a spring 122 is connected or bears against. The spring 122 is a coil spring that encircles the septum activator 74*e*, preferably in at least the proximal section 88 of the activator.

As shown in FIG. 13, in an at-rest position, the septum activator 74*e* fits within the catheter adapter 20 with the distal end 76 of the activator 74*e* proximal and adjacent the proximal face 119 of the septum 110 (which, in the illustrated embodiment, is sealingly retained in a seat 58 defined in the inner surface 59 of the adapter 20). A distal end of the spring 122 is proximal the stationary arm 120 and adjacent a contact surface 124 of the arm 120.

With reference next to FIG. 14, when a coupler 100 is attached, the coupler extension 104 engages the proximal end 80 of the activator 74*e*, urging the activator distally so as to force the septum 110 into an open configuration, establishing a fluid flow path F. The illustrated activator 74*e* is rigid or semi-rigid so as not to compress substantially when moved distally.

As the coupler extension 104 urges the activator 74*e* distally, the spring 122 engages the contact surface 124 of the arm 120, and is compressed between the contact surface 124 and the flange 95. When the coupler extension 104 is removed, the compressed spring 122 tends to expand, and exerts a proximally-directed force so as to urge the activator 74*e* proximally, out of engagement with the septum 110 and to the at-rest position. As such, the septum 110 can again close to reseal, and the activator 74*e* is poised to repeat the process upon connection of another coupler 100.

It is to be understood that additional embodiments may employ somewhat different structure. For example, in another embodiment, a movable member may be arranged within the catheter adapter 20 and interposed between the coupler extension 104 and the proximal end 80 of the catheter adapter 74*e*. The spring may be interposed between the stationary arm 120 and the movable member. In still other embodiments, a proximal end of the spring may be attached to a portion of the catheter adapter, and a distal end of the spring may be attached to the activator, so that when the activator is forced distally by the coupler, the spring elongates and is placed in tension. When the coupler is removed, the spring thus pulls the activator proximally.

The embodiment illustrated in FIGS. 12-14 employs a coil spring. It is to be understood that other styles, sizes, etc. of springs can be used in other embodiments. For example, one or a plurality of cantilever-type springs, or a plurality of small coil springs can be employed. Also, some spring embodiments may comprise elastomeric materials such as one or a plurality of sponge-like members or synthetic rubber members. Any suitable spring structure, in which energy is stored in the spring as the activator is forced distally by the couple, which energy urges the activator proximally when the coupler is removed, can be employed. It is also to be understood that other configurations of the septum activator, such as configurations employing apertures, or multi-piece configurations, may be employed, and such configurations may enable flushing of both the distal and proximal chambers 70, 72 of the catheter adapter 20 when the coupler 100 attaches a source of flushing fluid such as an IV fluid.

Figure 15:
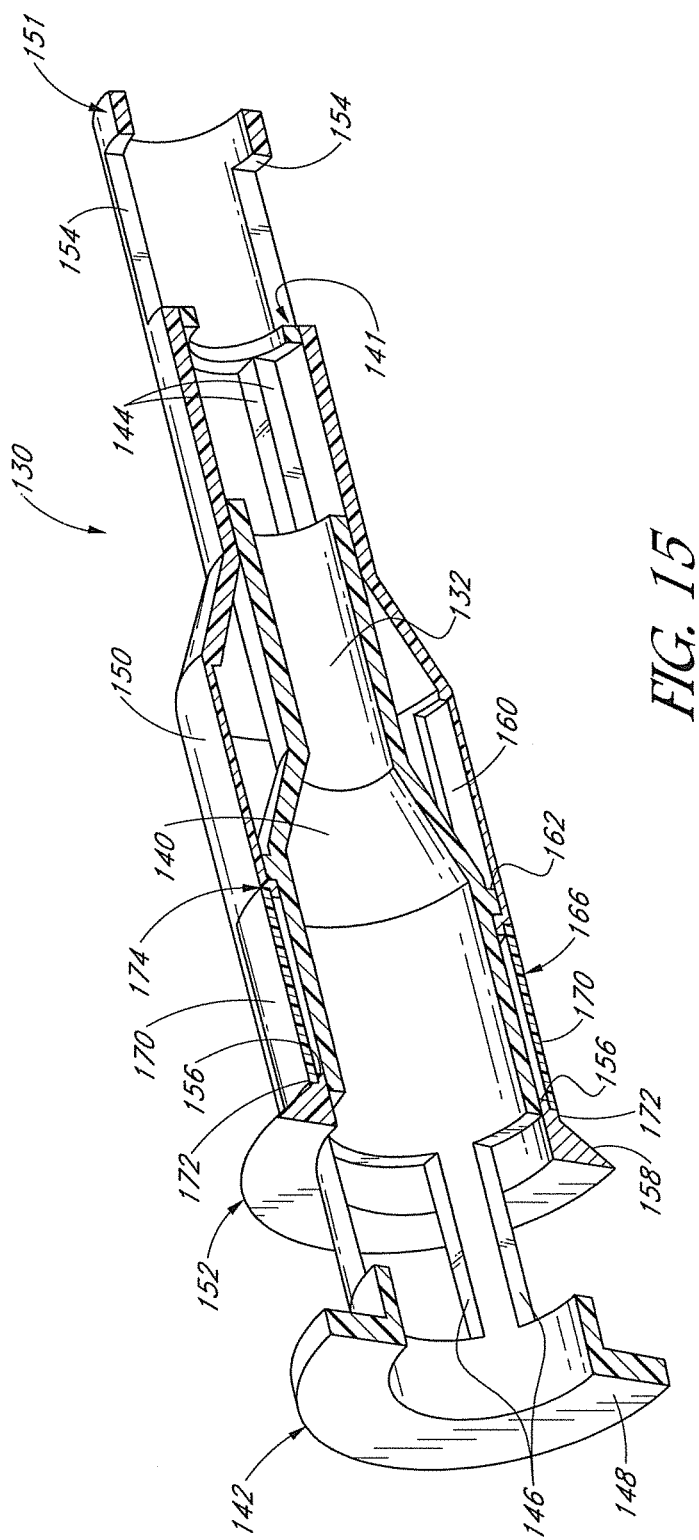
FIG. 15 is a perspective view of a septum activator in accordance with still another embodiment, shown in a first arrangement.
Figure 16:
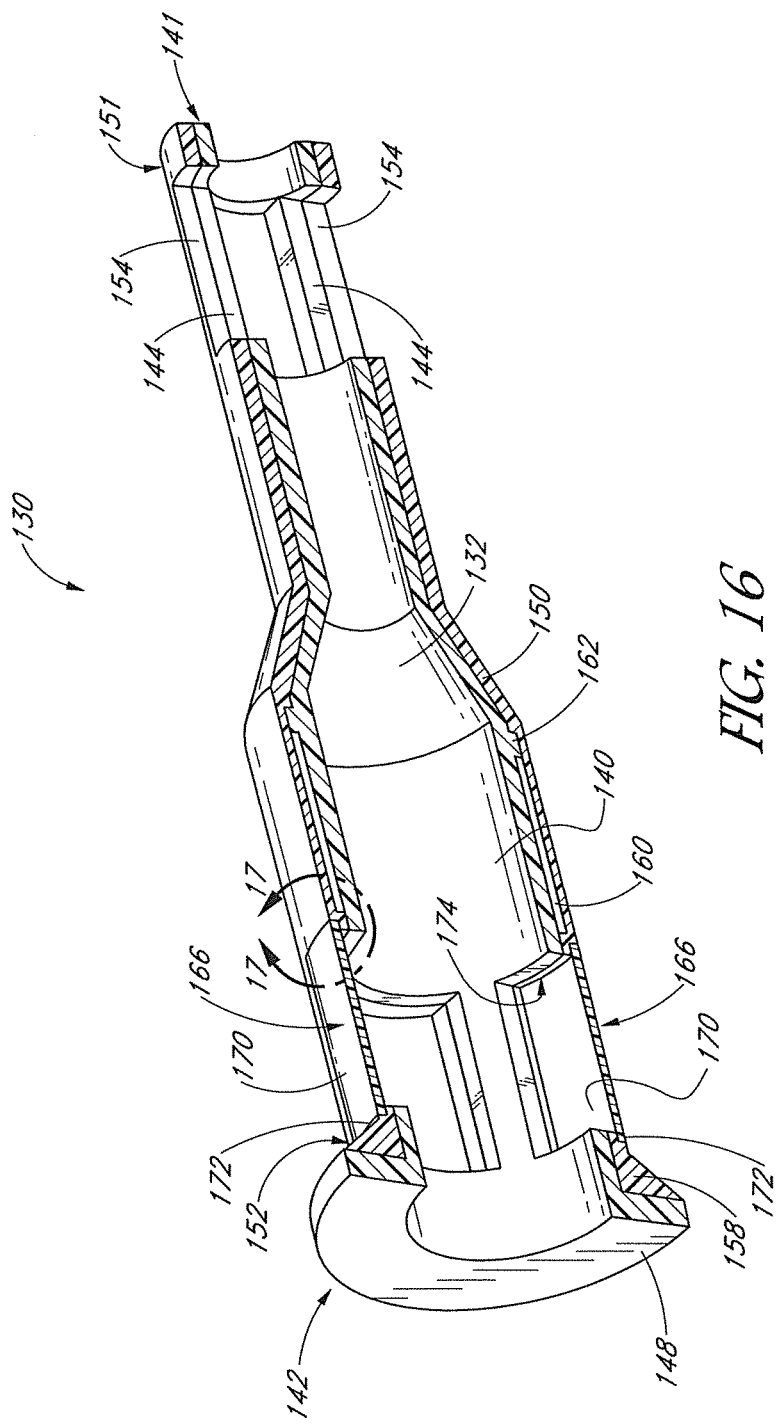
FIG. 16 shows the septum activator of FIG. 15 in a second arrangement.

With reference next to FIGS. 15 and 16, in accordance with another embodiment, a multi-piece septum activator 130 comprises an inner tubular body 140 and an outer tubular body 150. The inner tubular body 140 has a distal end 141 and a proximal end 142. Distal openings 144 are formed through a wall of the inner tubular body 140 near the distal end 141. Proximal openings 146 are formed through a wall of the inner tubular body 140 near its proximal end 142. A proximal flange 148 is formed at the proximal end 142 of the inner tubular body 140. The inner tubular body 140 defines an activator lumen 132.

The outer tubular body 150 also has a distal end 151 and a proximal end 152. Distal openings 154 are formed through a wall of the outer tubular body 150 near the distal end 151, and proximal openings 156 are formed through a wall of the outer tubular body 150 near its proximal end 152. A circumferential seal 158 extends radially outwardly at the proximal end 152 of the outer tubular body 150.

With continued reference to FIGS. 15 and 16, the inner and outer tubular bodies 140, 150 are arranged coaxially and movable relative one another between a first or blocked arrangement as shown in FIG. 15 and a second or aligned arrangement as shown in FIG. 16. In the aligned arrangement, the distal openings 144 of the inner tubular body 140 are aligned with the distal openings 154 of the outer tubular body 150 and the proximal openings 146 of the inner tubular body 140 are aligned with the proximal openings 156 of the outer tubular body 150. However, in the blocked arrangement, the openings of the inner and outer tubular bodies are not aligned. As such, fluids can flow through the openings 146, 156, 144, 154, when the activator 130 is in the aligned arrangement, but are blocked from flowing into or out of the activator lumen 132 when the activator 130 is in the blocked arrangement.

In the illustrated embodiment, a plurality of elongated recesses or tracks 160 can be formed in the outer tubular body 150, and complementary protuberances 162 can be formed on the inner tubular body 140. The protuberances 162 fit within the tracks 160, and maintain proper alignment when the tubular bodies 140, 150 move axially relative to one another. Preferably, the tracks 160 also define endpoints limiting relative movement of the tubular bodies between the blocked and aligned arrangements. It is to be understood, however, that in other embodiments the tubular bodies 140, 150 can be configured to move rotatably relative to one another between blocked and aligned arrangements.

Figure 17A:
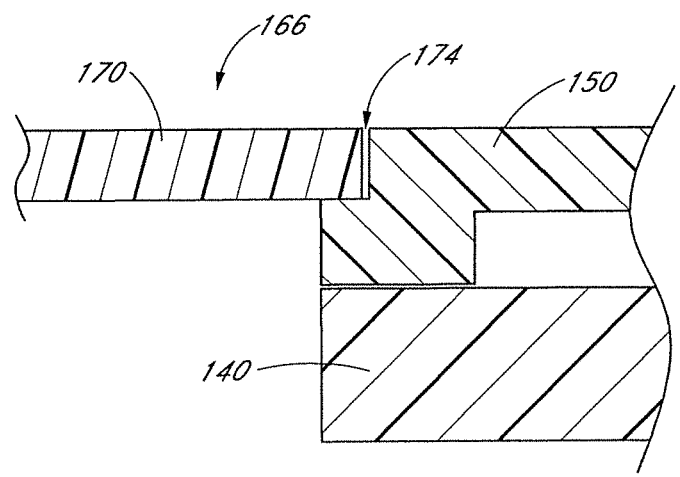
FIG. 17A is a cutaway view taken along line 17-17 of FIG. 16.

With continued reference to FIGS. 15 and 16, and additional reference to FIG. 17A, a one-way valve 166 is arranged at each of the proximal openings 156 of the outer tubular body 150. In the illustrated embodiment, each one-way valve 166 comprises a flap 170 that covers the associated proximal opening 156. Preferably, a proximal end of each flap 170 is hingedly connected to the outer tubular body 150 by a hinge 172 at or adjacent the proximal end of each proximal opening 156. The hinge 172 can comprise an elastomeric material or can, in additional embodiments, comprise any desired hinge structure. Similarly, each flap can comprise an elastomeric material, a rigid or semi-rigid material, or combinations thereof. Preferably, side and distal edges of each flap 170 are not attached to the outer tubular body 150, but the flap 120 is biased to urge the side and distal edges into engagement with the body 150. A flap receiver 174 can be configured to receive at least a distal edge of the flap 170. Each flap 170 can hingedly open outwardly, but is prevented by the flap receiver 174 from hingedly opening in an inward direction. As such, each flap 170 forms a one-way valve, tending to open to allow fluids to flow out of the lumen 132 through the associated proximal opening 156 but tending to close to prevent fluids from flowing inwardly through the proximal opening 156.

Figure 17B:
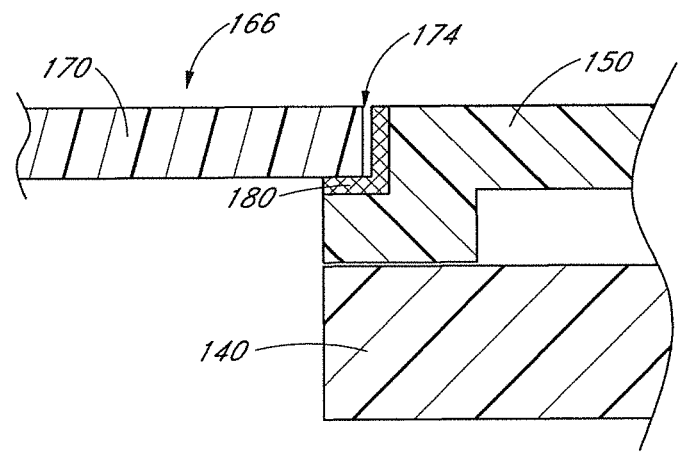
FIG. 17B depicts another embodiment shown from the same view as in FIG. 17A.
Figure 17C:
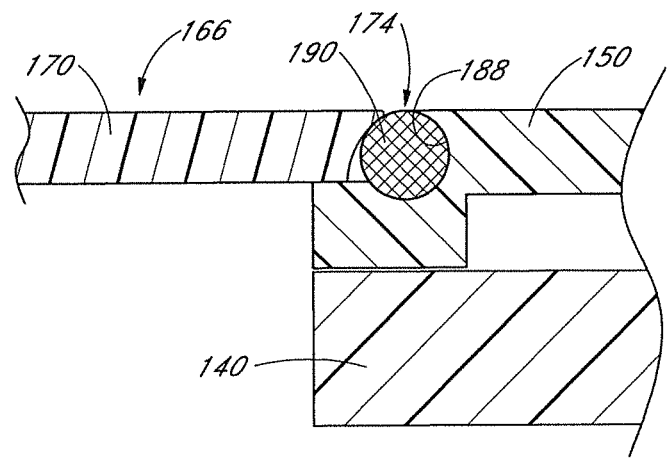
FIG. 17C depicts yet another embodiment shown from the same view as in FIG. 17A.

With specific reference to FIG. 17A, in one embodiment, the flap receiver 174 comprises a cutout portion of the outer tubular body 150. In this embodiment, the outer surface of the flap is aligned with the outer surface of the tubular body 150. It is to be understood that, in other embodiments, the flap can engage and form a seal with the associated tubular body using other structures. For example, the flap can rest atop the outer surface of the associated tubular body without any notch or other receiving structure being formed therein. In another embodiment represented in FIG. 17B, a layer of a hydrophobic material 180 can be applied to the flap receiver 174, providing additional resistance to fluid passing between the flap 170 and the receiver 174. In yet additional embodiments, an inner surface of the flap, or portions of both and outer surface and inner surface of the flap can be coated with a layer of hydrophobic material in addition to or instead of the layer 180 applied to the flap receiver 174. The hydrophobic layer 180 can be made from any of a number of suitable materials well known to those skilled in the art, such as super hydrophobic polyvinyldiflouride (PVDF). With specific reference next to FIG. 17C, in yet another embodiment, the flap receiver 74 can comprise a seal seat 188 configured to receive and hold a seal such as an O-ring 190. In such an embodiment, the flap 170 closes upon the O-ring 190 so as to effect a seal.

Figure 18:
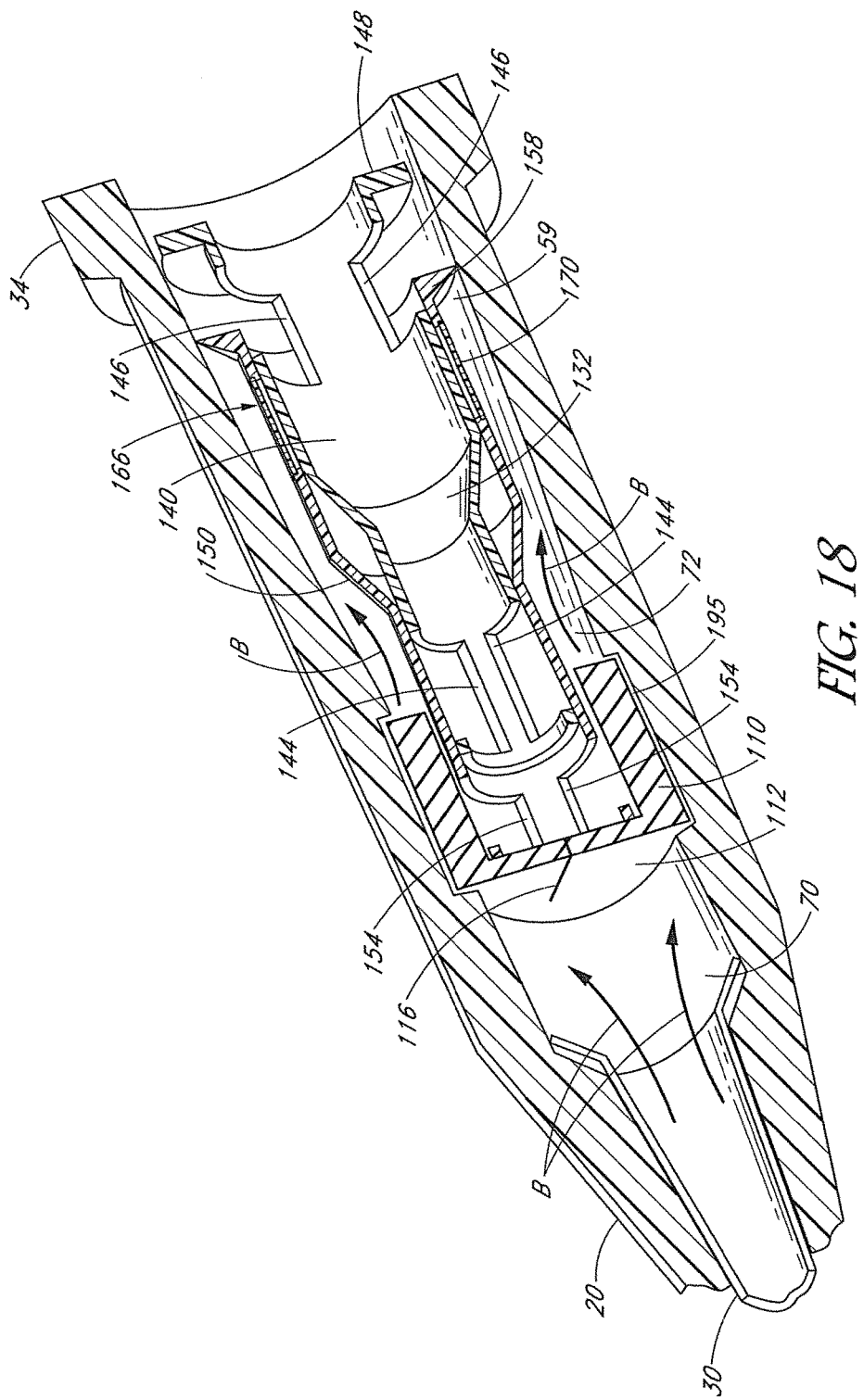
FIG. 18 is a cutaway view showing another embodiment of a catheter adapter employing a septum activator as in FIGS. 15-16.

With reference next to FIG. 18, the multi-piece activator 130 can be placed in the proximal chamber 72 of the catheter adapter 20. Preferably, the multi-piece activator 130 is initially disposed in the blocked arrangement as shown. In some embodiments, one or more vents 195 can be formed around the septum 110. As such, a portion of flashback blood B that enters the distal chamber 70 can flow through the vents 195 and into the proximal chamber 72. In some embodiments, the proximal chamber 72 may operate as a viewing window through which a clinician can detect flashback blood B. Preferably, the seal 158 of the outer tubular body 150 engages the inner surface 59 of the catheter adapter 20 so as to prevent blood from flowing therethrough and, possibly, out of the catheter adapter 20. Since the multi-piece activator 130 is in the blocked arrangement, blood B is blocked from flowing into the lumen 132.

Figure 19:
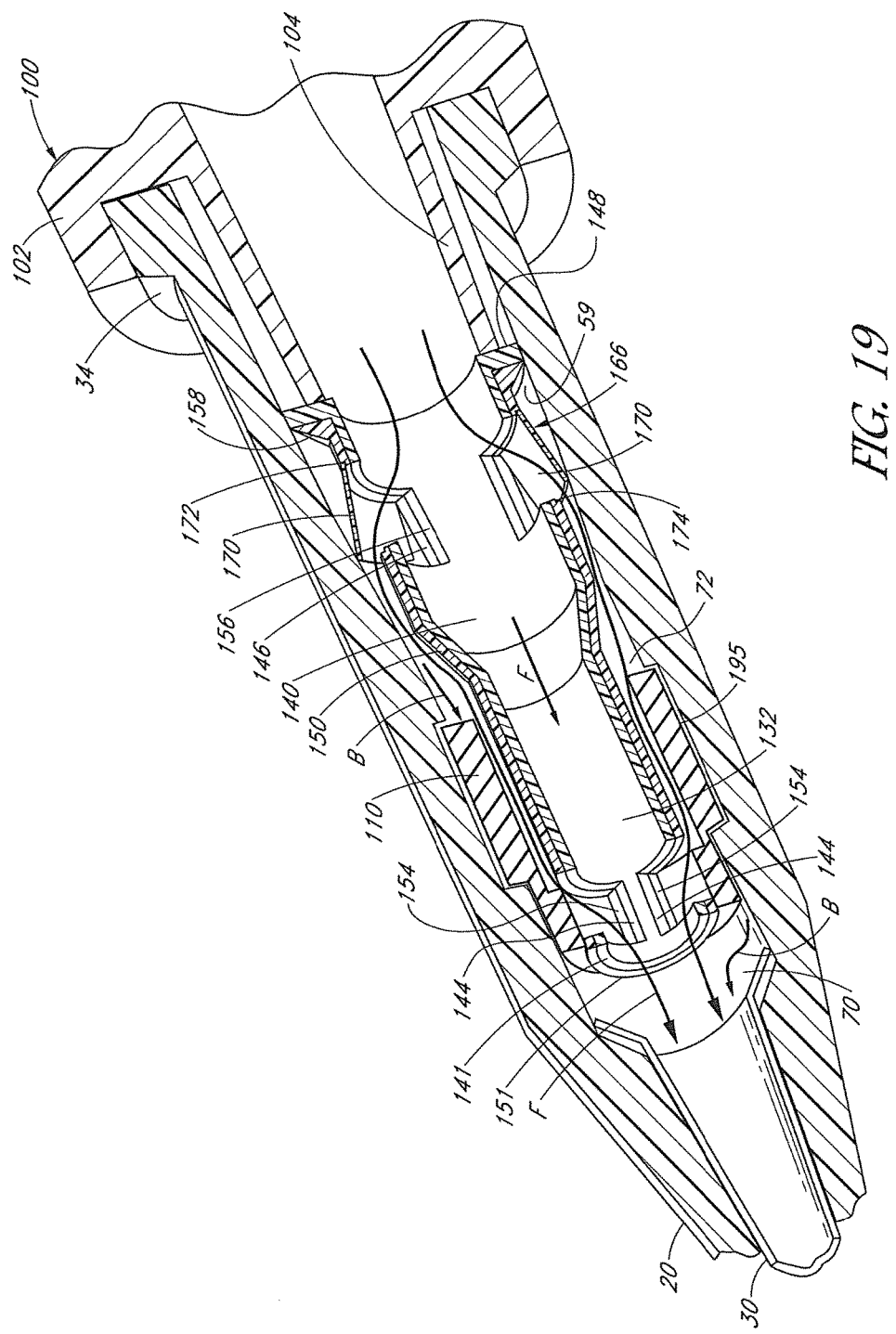
FIG. 19 shows the arrangement of FIG. 18 with a coupler attached.

With additional reference to FIG. 19, when a coupler 100 such as a luer coupler is connected to the proximal flange 34, the extension 104 of the coupler will engage the proximal flange 148 and urge the inner tubular body 140 distally relative to the outer tubular body 150 until the tubular bodies are in the aligned arrangement. Once the tubular bodies are in the aligned arrangement, they will move distally together relative to the catheter adapter 20 so that their aligned distal ends 141, 151 engage and deform the septum 110, breaking the seal and establishing a fluid flow path therethrough.

FIG. 19 illustrates an embodiment in which the coupler 100 is connected to a source of medical fluids such as IV fluids F. As shown, IV fluids F are delivered distally through the activator lumen 132 and open septum 111 and into the catheter tube 30 for delivery to the patient. Also, the pressure of the fluids F being delivered to the activator 130 forces the flaps 170 to open so that fluids F flow out of the lumen 132 through the aligned proximal openings 146, 156, into and through the proximal chamber 72, and then back into the lumen 132 through the aligned distal openings 144, 154. As such, flashback blood B within the proximal chamber 72 can be flushed out of the chamber 72 by the IV fluids F.

In additional embodiments, a septum activator that does not have inner and outer tubular bodies employs a single tubular body with both proximal and distal openings and a one-way valve arranged at the proximal openings.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses the invention and obvious modifications and equivalents thereof. For example, a method of making a catheter assembly as described herein, as well as a method of using such an assembly, is contemplated. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

1. A catheter assembly, comprising:
   a catheter adapter having a distal end and a wall surface defining an internal space;
   a catheter tube extending from the distal end of the catheter adapter;
   a septum disposed within the internal space of the catheter adapter, the septum dividing the internal space of the catheter adapter into a distal chamber and a proximal chamber; and
   a septum activator located in the Internal space of the catheter adapter and having a proximal end, a distal end, a length between the proximal end and the distal end of the septum activator, a proximal section proximate the proximal end of the septum activator, a distal section proximate the distal end of the septum activator, a first position in the internal space, and a second position in the internal space; the proximal section comprising an elastically compressible portion and a surface for pushing against by a coupler, and the distal section being more rigid than the proximal section;
   a needle attached to a needle hub, said needle comprising a needle shaft and a needle tip and the needle shaft extending through the catheter adapter, the septum activator, the septum, and the catheter tube in a ready to use position in which the needle tip extends out a distal end of the catheter tube;
   wherein the length of the septum activator in the first position is a first position length and the length of the septum activator in the second position is a second position length, which is shorter than the first position length;
   wherein the elastically compressible portion of the septum activator, in the first position, is configured to be compressed to a compressed state in which the length of the septum activator is shortened to the second position length when a coupler contacts and applies a force in the distal direction to the proximal end of the septum activator so as to urge the distal end of the septum activator against the septum to deform the septum and move the septum activator to the second position; and
   wherein the elastically compressible portion of the septum activator elastically expands and the septum activator lengthens from the compressed state and from the second position length when the coupler is removed from contact with the septum activator.

2. The catheter assembly as in claim 1, wherein the elastically compressible portion of the septum activator comprises a plurality of elongate, spaced apart legs configured to deflect when the coupler applies the force to the septum, thereby decreasing an axial length of the elastically compressible portion.

3. The catheter assembly as in claim 1, wherein an aperture is formed between adjacent spaced apart legs.

4. The catheter assembly as in claim 3, wherein the spaced apart legs extend a majority of the length of the septum activator.

5. The catheter assembly as in claim 1, wherein an expansion groove is formed in the proximal chamber of the catheter adapter, the expansion groove having a distal end, and a portion of the elastically compressible portion applies a force against the distal end of the expansion groove in opposition to the force applied by the coupler in the distal direction.

6. The catheter assembly as in claim 5, wherein the plurality of elongate, spaced apart legs extend a majority of the length of the septum activator.

7. A catheter assembly, comprising:
   a catheter adapter having a distal end and a wall surface defining an internal space;
   a septum comprising at least one slit located in the internal space of the catheter adapter;
   a catheter tube extending from the distal end of the catheter adapter;
   a septum activator located in the internal space of the catheter adapter and having a proximal end that is movable between an at rest position and an actuated position, a compressible portion, a distal end, and a nose section at the distal end of the septum activator for opening the at least one slit if the septum;

a needle attached to a needle hub, said needle comprising a needle shaft and a needle tip and the needle shaft extending through the catheter adapter, the septum activator, the septum, and the catheter tube in a ready to use position in which the needle tip extends out a distal end of the catheter tube;

wherein a location, relative to the septum, of the proximal end of the septum activator at the at rest position is proximal of a location, relative to the septum, of the proximal end of the septum activator at the actuated position;

wherein the compressible portion has a proximal end and a distal end and a length between the proximal end and the distal end of the compressible portion, the compressible portion is configured to be compressed to a compressed configuration in which the length of the compressible portion is reduced when a coupler contacts and applies a distal force to the proximal end of the septum activator so as to urge the septum activator distally into the septum to deform the septum; and wherein the catheter adapter further comprises a shoulder formed in the internal space of the catheter adapter to be abutted by the compressible portion when the septum activator is positioned in at least the actuated position.

8. The catheter assembly as in claim 7, further comprising a movable member figured to be moved with the septum activator and wherein the movable member is integrally formed with the septum activator.

9. A catheter assembly, comprising:
a catheter adapter having a distal end and a wall surface defining an internal space;
a septum located in the internal space of the catheter adapter and comprising at least one slit; a catheter tube extending from the distal end of the catheter adapter;
a septum activator located in the internal space of the catheter adapter, the septum activator having a septum activator lumen and comprising a proximal end, a distal end, a proximal opening proximate the proximal end, a distal opening at the distal end, and a compressible portion adjacent the proximal end;
a shoulder in the internal space abutted by a distal surface of the septum to fix an outer perimeter of the septum from axial movement;
a needle attached to a needle hub, said needle comprising a needle shaft and a needle tip and the needle shaft extending through the catheter adapter, the septum activator, the septum, and the catheter tube in a ready to use position in which the needle tip extends out a distal end of the catheter tube;
wherein the compressible portion of the septum activator in an at rest configuration is configured to be compressed into a compressed configuration when a coupler contacts and applies a force to the proximal end of the septum activator so as to urge the septum activator into the septum so as to deform the septum and form a fluid pathway through the septum activator lumen and the at least one slit;
wherein a length of the septum activator between the proximal end of the septum activator and the distal end of the septum activator in the compressed configuration is less than a length of the septum activator between the proximal end of the septum activator and the distal end of the septum activator in the at rest configuration; and
wherein when the coupler is removed from contact with the septum activator, the compressible portion elastically expands from the compressed configuration to the at rest configuration.

10. The catheter assembly as in claim 9, wherein the septum defines a one-way check valve and wherein the one-way check valve comprises a hinged flap.

11. The catheter assembly as in claim 9, wherein the septum activator comprises a distal side opening formed through a side wall and spaced distally from a proximal side opening.

12. The catheter assembly as in claim 11, wherein a blood flashback chamber is defined between a side wall of the septum activator and an inner surface of the catheter and wherein distally-directed fluid flow can flow from the flashback chamber through the distal side opening and back into the septum activator lumen.

13. The catheter assembly as in claim 10, wherein the one-way valve comprises a hydrophobic surface.

* * * * *

UNITED STATES PATENT AND TRADEMARK OFFICE
CERTIFICATE OF CORRECTION

PATENT NO. : 9,919,136 B2
APPLICATION NO. : 14/550398
DATED : March 20, 2018
INVENTOR(S) : Siew Ping Lim et al.

It is certified that error appears in the above-identified patent and that said Letters Patent is hereby corrected as shown below:

In the Specification

In Column 7, Line 24, delete "Luer." and insert -- luer. --, therefor.

In Column 10, Line 46, delete "polyvinyldiflouride" and insert -- polyvinyldifluoride --, therefor.

In the Claims

In Column 11, Line 63, in Claim 1, delete "Internal" and insert -- internal --, therefor.

Signed and Sealed this
Sixteenth Day of August, 2022

Katherine Kelly Vidal
*Director of the United States Patent and Trademark Office*